US 6,549,122 B2

United States Patent
Depta

(10) Patent No.: US 6,549,122 B2
(45) Date of Patent: Apr. 15, 2003

(54) PORTABLE ORIENTATION SYSTEM

(75) Inventor: Robert Depta, Augsburg (DE)

(73) Assignee: Fujitsu Siemens Computers GmbH, Augsburg (DE)

(*) Notice: Subject to any disclaimer, the term of this patent is extended or adjusted under 35 U.S.C. 154(b) by 0 days.

(21) Appl. No.: 09/935,357

(22) Filed: Aug. 22, 2001

(65) Prior Publication Data

US 2002/0067271 A1 Jun. 6, 2002

(30) Foreign Application Priority Data

Aug. 22, 2000 (DE) .......................... 100 41 085

(51) Int. Cl.[7] ................................. H04B 3/36
(52) U.S. Cl. ................... 340/407.1; 340/573.1; 340/540; 359/618; 359/630
(58) Field of Search .................. 340/407.1, 573.1, 340/5.8, 5.81, 540, 5.83, 5.82; 359/618, 630; 434/116, 112, 114

(56) References Cited

U.S. PATENT DOCUMENTS

| | | | | |
|---|---|---|---|---|
| 6,091,546 A | * | 7/2000 | Spitzer | ........................ 359/618 |
| 6,198,395 B1 | * | 3/2001 | Sussman | .................. 340/573.1 |
| 6,392,540 B1 | * | 5/2002 | Brown | ........................ 340/540 |

FOREIGN PATENT DOCUMENTS

| | | |
|---|---|---|
| DE | 44 02 764 C2 | 2/1996 |
| DE | 195 10 223 A1 | 2/1996 |
| DE | 198 24 479 A1 | 1/2000 |
| DE | 198 53 915 A1 | 5/2000 |
| WO | WO 98/37691 | 8/1998 |

* cited by examiner

*Primary Examiner*—Daryl Pope
(74) *Attorney, Agent, or Firm*—Laurence A. Greenberg; Werner H. Stemer; Ralph E. Locher

(57) ABSTRACT

A portable orientation system which, when for example the human sense of vision fails, can make information gathered from the surroundings available to another human sense. The portable orientation system has a sensor unit for selectively sensing information on the surroundings which is normally sensed by human senses. A signal processing unit is connected to the sensor unit and processes the signals of the sensor unit. A control module controls sensing options and/or processing options and/or output options of the sensor, the signal processing unit and the output unit. The portable orientation system further includes a power supply unit.

13 Claims, 2 Drawing Sheets

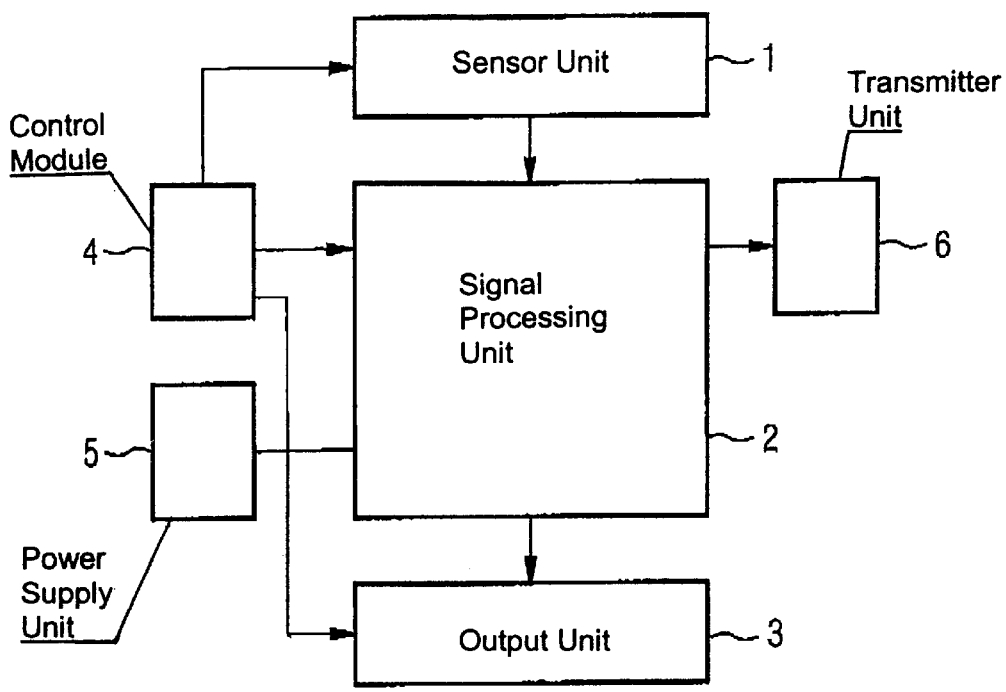
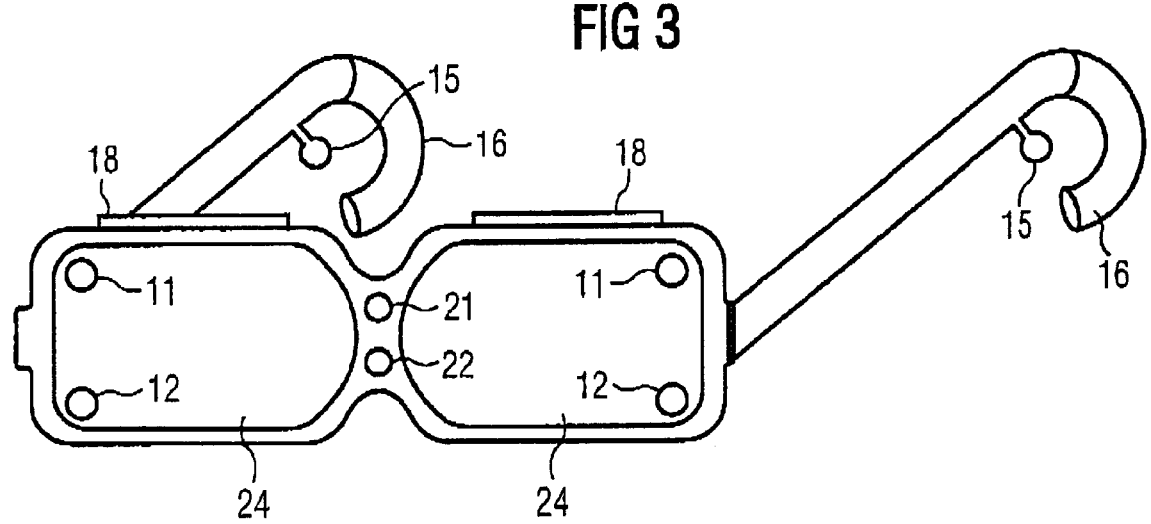

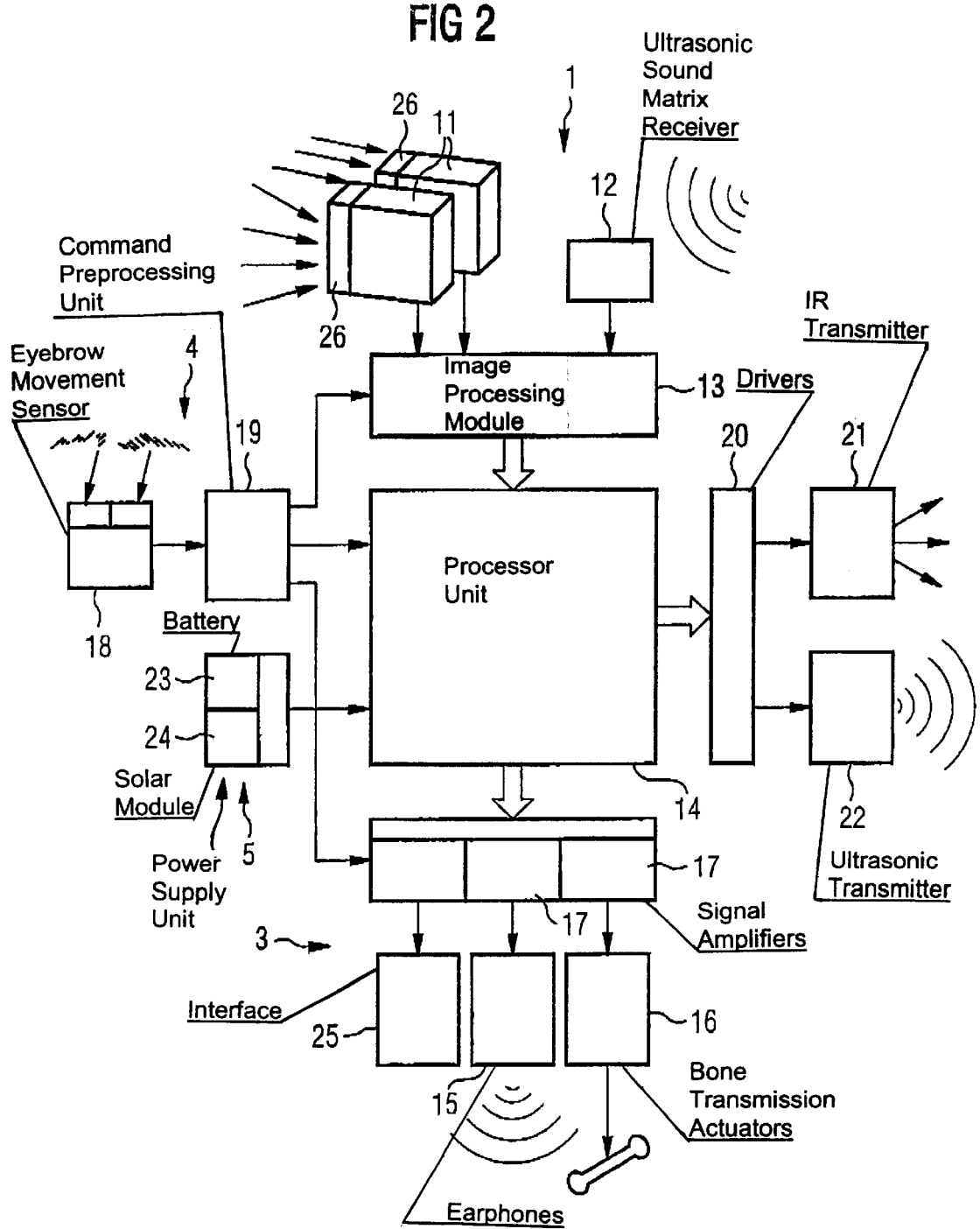

PORTABLE ORIENTATION SYSTEM

BACKGROUND OF THE INVENTION

Field of the Invention

The invention relates to a portable orientation system which, when for example the human sense of vision fails, can make information gathered from the surroundings available to another human sense.

In blind people, the brain centers which are responsible for sensory perception and hearing are particularly active. A large amount of information on the surroundings which cannot be perceived consciously by people with normal vision is sensed by blind people and is used as an orientation aid. Thus, even in the Middle Ages a method of acoustic orientation, based on the reflection of sound from objects in the surroundings, was practiced in various regions of Europe. The noises necessary for echo generation, for example clicking or snapping noises, were produced with the tongue or by knocking together two hard pieces of wood. According to the information available, blind people could in this way detect obstacles, for example trees, with a diameter of over 10 cm, even in the open air after a learning phase of only a few months.

Examples of orientation in the surroundings using sensors other than vision are also known from the animal world. For example bats emit ultrasonic sound waves, sense the reflections of these waves and use them to determine their surroundings. However, due to a lack of hearing sensitivity in this frequency range, it is not possible for humans to orientate themselves in this way.

SUMMARY OF THE INVENTION

It is accordingly an object of the invention to provide a portable orientation system which makes it possible, given the failure of a sense, to orient oneself in unfamiliar surroundings or to orientate oneself in surroundings under conditions in which orientation is normally not possible for a human being.

With the foregoing and other objects in view there is provided, in accordance with the invention, a portable orientation system, including:

- a sensor unit configured to selectively sense information on surroundings that is normally sensed by human senses;
- a signal processing unit connected to the sensor unit and processing signals supplied by the sensor unit;
- an output unit operatively connected to the signal processing unit;
- a control module for controlling at least one option selected from the group consisting of a sensing option for the sensor unit, a processing option for the signal processing unit, and an output option for the output unit; and
- a power supply unit connected to the signal processing unit.

In other words, the object of the invention is achieved with a portable orientation system having a sensor unit for selectively sensing information on the surroundings which is normally sensed by human senses, a signal processing unit which is connected to the sensor unit and has the purpose of processing the signals of the sensor unit, an output unit which transmits the information on the surroundings to the human senses and which is connected to the signal processing unit, a control module for controlling sensing and/or processing and/or output options of the sensor, the signal processing unit and the output unit, and a power supply unit.

The orientation system according to the invention can sense information gathered from the surroundings and convert it in such a way that different senses can access it. A significant field of application is the provision of support for visually impaired or blind people. In a favorable embodiment, a stereoscopic image detection unit, which operates either according to the visual (optical) or auditory (acoustic) principle, collects the information on the surroundings and passes it to the signal processing unit. Loudspeakers or earphones which enable the information on the surroundings to be accessed using the sense of hearing are the primary possibilities as an output unit. Another advantageous possibility, in particular for deaf and blind people, includes vibration transmission elements which, for example, transmit vibrations via bones or via inductive coupling to cochlea apparatus prostheses.

The control module permits various system components to be controlled. In this way, perception can be controlled in accordance with the positioning of the eyeballs and the focusing on a near or distant object in sighted people. Advantageous control of the control module is carried out through the use of movements of the eyebrows which are sensed through the use of sensors. When the information on the surroundings is sensed visually, video cameras are used, but it is also possible to use ultrasonic sound receivers if they are combined with an ultrasonic sound transmitter so that the system evaluates the echo. Video cameras can also operate in the infrared range. They are advantageously combined with infrared transmitters.

Thus, according to a preferred feature of the invention, the sensor unit includes at least one video camera, and the signal processing unit includes an image detection unit for detecting or recognizing objects based on the information on the surroundings. The at least one video camera preferably has a filter unit.

By using sensors for infrared light or ultrasonic sound it is also possible to expand the perception spectrum of normally sighted people.

According to another feature of the invention, an ultrasonic sound transmitter is provided and the sensor unit has an ultrasonic sound receiver.

According to yet another feature of the invention, an infrared transmitter is provided and the at least one video camera is sensitive to infrared light.

According to a further feature of the invention, the output unit has vibration actuators.

According to yet a further feature of the invention, the control module has movement sensors for sensing eyebrow movements.

It is advantageous if all components of the system are integrated in a spectacle frame so that the orientation system can be carried comfortably and inconspicuously.

Other features which are considered as characteristic for the invention are set forth in the appended claims.

Although the invention is illustrated and described herein as embodied in a portable orientation system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a simplified block circuit diagram of an orientation system according to the invention;

FIG. 2 is a detailed block circuit diagram of an orientation system according to the invention; and FIG. 3 is a diagrammatic perspective view of an embodiment of the portable orientation system according to the invention configured as a pair of glasses.

DESCRIPTION OF THE PREFERRED EMBODIMENTS

Referring now to the figures of the drawings in detail and first, particularly, to FIG. 1 thereof, there is illustrated the basic method of operation of the portable orientation system with reference to a block circuit diagram. Information on the surroundings is sensed through the use of a sensor unit 1. This information gathered from the surroundings which is present in electronic form is passed on to a signal processing unit 2. In the signal processing unit, the electronic information is processed, wherein objects in the surrounding area are detected and the information is further processed in such a way that it can be fed to an output unit 3. In this way, the detected objects are transmitted to a human sense. After a learning and familiarization period, the brain can interpret the stimuli which are transmitted and can use the stimuli to reconstruct the same picture of the surroundings as is perceived by people having eyesight. A control module 4 can be used to set options of the sensor unit 1, the signal processing unit 2 and the output unit 3. With respect to the sensor unit 1 these options are, for example, filter units in visual video cameras and zoom settings, with respect to the signal processing unit these options are also zoom settings and the reproduction of contrasts and other adjustable parameters of an image processing unit. With respect to the output unit, it must be possible to set the signal volume for earphones or the vibration amplitudes for vibration actuators. Because the system is intended to be a portable orientation system, it is necessary to supply a power supply unit 5. The combination of a power supply based on a battery and supported by solar modules is advantageous.

Additional advantages are obtained if a transmitter unit 6 is added, for example an infrared transmitter or an ultrasonic sound transmitter in order to permit appropriate sensors 1 to perceive the surrounding environment under conditions, for example, in the dark, in which orientation is normally not possible.

FIG. 2 shows the block circuit diagram of FIG. 1 in a more detailed form. In this case, various methods for detecting or recognizing the surroundings are combined. The sensor unit 1 has both visual video cameras 11 and an ultrasonic sound matrix receiver 12. In order to be able to generate a three-dimensional image, at least two video cameras are necessary. The video cameras have filter units 26 with color, polarization and infrared filters. The filter unit 26 is placed directly in front of the lenses of the video cameras 11 and accommodated in a lens module together with the lenses. The different filters 26 permit the obstacles to be detected or objects to be localized or positioned under different ambient conditions, and allow the perception of even persons with eyesight to be expanded. The data sensed by the sensor unit 1 is passed on to an image processing module 13. This module firstly detects the individual objects and their boundary with respect to the background, changes the contrast between the objects in accordance with the settings by the control module 4, converts this information into a virtual three-dimensional image by reference to the slight differences between the detected images of the two video cameras, and combines the information of the visual system 11 and of the ultrasonic sound system 12. The 3D information supplied by the image processing module 13 is firstly decoded in the downstream processor unit 14 and then prepared individually for a left-hand and a right-hand earphone 15, or for the bone transmission actuators 16. This information is passed on to the signal amplifiers 17 provided for the different actuators 15 and 16.

The conversion in the processor unit 14 is carried out in this exemplary embodiment in such a way that relatively small objects are depicted with relatively high tones, and relatively large objects are depicted with relatively low tones. In order to encode the distance information, relatively large amplitudes are used for close objects and relatively small amplitudes for distant objects. In an adaptation phase, a diagram for volume and frequency is generated in accordance with the audible spectrum and the sensitivity of the individual to volume, and is stored in the device as a user profile. In this way, an optimum device setting can be defined in accordance with the individual perception characteristic. Instead of the abovementioned assignment or allocation between information on the surroundings and the generation of stimuli, other assignments or allocations may also be selected, but the abovementioned assignment is the physiologically most favorable.

In order to control the settings, an eyebrow movement sensor 18 is provided which controls the individual modules of the system in accordance with the corresponding decoding and detection of data through the use of a command preprocessing unit 19. The processor unit 14 actuates the transmitter units 21 and 22 for infrared light or for ultrasonic sound through the use of corresponding amplifiers and drivers 20. A battery 23 and a solar module 24 are provided to supply the system with power. In addition, there is an interface 25 integrated into the system for accessories.

For people with normal hearing, transmission via bones has the advantage that it always supplies understandable signals irrespective of background noise and does not impede the sensing of other audible information. Using both systems simultaneously, namely transmission of sound by air and via bone, makes it possible to place the audibly imaged elements precisely in an acoustic three-dimensional space built up by the brain.

FIG. 3 shows a possible embodiment of the system as a pair of glasses. The modules are integrated with a spectacle frame. Here, solar modules 24 are provided where the lenses would normally be located. On the respective outer side of the solar modules 24 there is, in each case, a video camera 11 and an ultrasonic matrix receiver 12. The infrared transmitter 21 and the ultrasonic sound transmitter 22 are disposed in the center above the nose support face. The eyebrow movement sensors 18 are provided at the upper edge of the frame. The electronic elements for image processing, the processor and the amplifiers for the output unit are accommodated in the spectacle frame or in the arms of the spectacle frame. Currently available semiconductor technology makes it possible to manufacture all the electronic elements in such a way that high-quality image processing and conversion is possible in real time. The vibration actuators 16 for transmission of sound via bone are provided in the rear region of the arms of the glasses, where the transmission to the bones behind the flap of the ear (outer ear) takes place. Small earphones 15 are also attached to the arm of the glasses. Elements for inductive coupling in deaf and blind people with cochlea apparatus prostheses are not illustrated in this exemplary embodiment, but can be integrated without difficulty in a similar way to the vibration actuators.

I claim:

1. A portable orientation system, comprising:

a sensor unit configured to selectively sense information on spatial surroundings that is normally sensed by human senses;

a signal processing unit connected to said sensor unit and processing signals supplied by said sensor unit;

an actuator transmitting the information on spatial surroundings for reception by an acoustic human sense, said actuator being operatively connected to said signal processing unit;

a control module for controlling at least one option selected from the group consisting of a sensing option for said sensor unit, a processing option for said signal processing unit, and an output option for said actuator; and a power supply unit connected to said signal processing unit.

2. The portable orientation system according to claim 1, wherein:

said sensor unit includes at least one video camera; and said signal processing unit includes an image detection unit for detecting objects based on the information on the surroundings.

3. The portable orientation system according to claim 2, wherein said at least one video camera has a filter unit.

4. The portable orientation system according to claim 1, including:

an ultrasonic sound transmitter operatively connected to said signal processing unit; and said sensor unit having an ultrasonic sound receiver.

5. The portable orientation system according to claim 2, including:

an infrared transmitter operatively connected to said signal processing unit; and said at least one video camera being sensitive to infrared light.

6. The portable orientation system according to claim 1, wherein said actuator is one of two actuators, one of said two actuators is an earphone which transmits via sound the information on spatial surroundings, and another one of said two actuator is a bone vibrator which transmits via a human bone the information on spatial surroundings.

7. The portable orientation system according to claim 1, wherein said control module has movement sensors for sensing eyebrow movements.

8. The portable orientation system according to claim 1, wherein said sensor unit, said signal processing unit, said actuator, said control module, and said power supply unit are configured to be integrated into a spectacle frame.

9. The portable orientation system according to claim 1, wherein said power supply unit includes a solar module.

10. The portable orientation system according to claim 2, wherein:

said at least one video camera includes at least two video cameras providing image information; and said image detection unit generates a three-dimensional image from the image information provided by said at least two video cameras.

11. A portable orientation system, comprising:

a spectacle frame;

a sensor unit configured to selectively sense information on spatial surroundings that is normally sensed by human senses;

a signal processing unit connected to said sensor unit and processing signals supplied by said sensor unit;

an actuator transmitting the information on spatial surroundings for reception by an acoustic human sense, said actuator being operatively connected to said signal processing unit;

a control module for controlling at least one option selected from the group consisting of a sensing option for said sensor unit, a processing option for said signal processing unit, and an output option for said output unit;

a power supply unit connected to said signal processing unit; and said sensor unit, said signal processing unit, said actuator, said control module, and said power supply unit being integrated into said spectacle frame.

12. The portable orientation system according to claim 1, wherein relatively small objects are depicted with relatively high tones, and relatively large objects are depicted with relatively low tones by said actuator.

13. The portable orientation system according to claim 11, wherein relatively small objects are depicted with relatively high tones, and relatively large objects are depicted with relatively low tones by said actuator.

* * * * *